(12) United States Patent
Kiefer et al.

(10) Patent No.: US 9,116,155 B2
(45) Date of Patent: Aug. 25, 2015

(54) METHODS FOR EARLY DIAGNOSIS OF ACUTE CORONARY SYNDROME

(75) Inventors: Charles R. Kiefer, Shrewsbury, MA (US); L. Michael Snyder, Framingham, MA (US); Rachel E. Stock, Worcester, MA (US)

(73) Assignee: University of Massachusetts, Boston, MA (US)

( * ) Notice: Subject to any disclaimer, the term of this patent is extended or adjusted under 35 U.S.C. 154(b) by 1271 days.

(21) Appl. No.: 12/481,970

(22) Filed: Jun. 10, 2009

(65) Prior Publication Data

US 2009/0312952 A1 Dec. 17, 2009

Related U.S. Application Data

(60) Provisional application No. 61/060,729, filed on Jun. 11, 2008.

(51) Int. Cl.
*G01N 33/48* (2006.01)
*G01N 33/68* (2006.01)

(52) U.S. Cl.
CPC .... *G01N 33/6887* (2013.01); *G01N 2333/4712* (2013.01); *G01N 2333/4737* (2013.01); *G01N 2800/324* (2013.01); *G01N 2800/60* (2013.01)

(58) Field of Classification Search
None
See application file for complete search history.

(56) References Cited

U.S. PATENT DOCUMENTS

| 7,482,174 | B2 * | 1/2009 | Kiefer et al. | 436/529 |
| 2005/0181386 | A1 * | 8/2005 | Diamond et al. | 435/6 |
| 2006/0057642 | A1 * | 3/2006 | Kiefer et al. | 435/7.1 |
| 2009/0312952 | A1 | 12/2009 | Kiefer et al. | |

OTHER PUBLICATIONS

Bassand et al. (European Heart Journal, 2007, 28, 1598-1660).*
DeFilippi et al. (JAMA, Jul. 16, 2003, vol. 290, No. 3, pp. 353-359).*
Heeschen et al. (JACC vol. 35, No. 6, 2000, pp. 1535-1542).*
Hamm et al. (N Engl J Med., 1997, 337(23):1648-53).*
Antman et al., "Cardiac-specific troponin I levels to predict the risk of mortality in patients with acute coronary syndromes," N. Engl. J. Med., 335:1342-1349 (1996).
Beckett et al., "Cardiovascular Disorders," In *Lecture Notes: Clinical Biochemistry*, 7th Edition, Oxford, UK: Blackwell Publishing, Ltd., Chapter 11, pp. 160-176 (2005).
Kim et al., "Opsonization of apoptotic cells and its effect on macrophage and T cell immune responses," Ann. NY Acad. Sci., 987:68-78 (2003).
Ridker, "Clinical application of C-reactive protein for cardiovascular disease detection and prevention," Circulation, 107:363-369 (2003).
Roongsriton et al., "Common causes of troponin elevations in the absence of acute myocardial infarction: incidence and clinical significance," Chest., 125:1877-1884 (2004).
Steenbergen et al., "Cytoskeletal damage during myocardial ischemia: changes in vinculin immunofluorescence staining during total in vitro ischemia in canine heart," Circ. Res., 60:478-486 (1987).
Van Eyk et al., "Breakdown and release of myofilament proteins during ischemia and ischemia/reperfusion in rat hearts: identification of degradation products and effects on the pCa-force relation," Circ. Res., :82:261-271 (1998).
Volanakis and Wirtz, "Interaction of C-reactive protein with artificial phosphatidylcholine bilayers," Nature, 281:155-157 (1979).
Wang and Sui, "Dissociation and subunit rearrangement of membrane-bound human C-reactive proteins," Biochem. Biophys. Res. Comm., 288:75-79 (2001).
Kiefer et al; Early verification of myocardial ischemia with a novel biomarker of acute tissue damage: C-reactive protein fractional forms; Clinica Chimica Acta; 2012; pp. 413:1536-1541.
Vincente Bodi and Juan Sanchis, "C-Reactive Protein in Acute Coronary Syndrome. Looking Back in Order to Move Forward", Rev Esp Cardiol., vol. 59, No. 5, pp. 418-420 (2006).
Charles R. Kiefer et al., "Early verification of myocardial ischemia with a novel biomarker of acute tissue damage: C-reactive protein fractional forms", Clinica Chimica Acta, vol. 413, pp. 1536-1541 (2012).
Charles R. Kiefer et al., "Pulse pressure-driven neutral lipid accumulation and correlative proinflammatory markers of accelerated atherogenesis", Atherosclerosis, vol. 183, pp. 17-24 (2005).
Katie O'Conor et al., "Myeloperoxidase and C-reactive protein in patients with cocaine-associated chest pain", American Journal of Emergency Medicine, vol. 31, pp. 664-669 (2013).
Kristian Thygesen et al., "Universal Definition of Myocardial Infarction", Circulation: Journal of the American Heart Association, pp. 2634-2653 (Nov. 27, 2007).
Agewall et al., "Troponin Elevation in Coronary Ischemia and Necrosis", Curr Atheroscler Rep., vol. 16:396 (2014).
Anand et al., "C-Reactive Protein in Heart Failure: Prognostic Value and the Effect of Valsartan", Circulation, vol. 112:1428-1434 (2005).
Bleier et al., Different intracellular compartmentations of cardiac troponins and myosin heavy chains: a causal connection to their different early release after myocardial damage, Clinical Chemistry, vol. 44:1912-1918 (1998).
Brenden et al., "Gray zone BNP levels in heart failure patients in the emergency department results from the Rapid Emergency Department Heart Failure Outpatient Trial (REDHOT) multicenter study", Am. Heart J, vol. 151:1006-1011 (2006).
Frick et al., "[Myocarditis and sudden cardiac death in athletes. Diagnosis, treatment, and prevention]", Herz, vol. 34:299-304 (2009).
Khreiss et al., Loss of Pentameric Symmetry of C-reactive Protein is Associated with Delayed Apoptosis of Human Neutrophils, J Biol Chem, vol. 277:40775-40781 (2002).
Kinoshita et al., "Elucidation of a protease-sensitive site involved in the binding of calcium to C-reactive protein", Biochemistry., vol. 28:9840-9848 (1989).

(Continued)

*Primary Examiner* — Pablo S Whaley
(74) *Attorney, Agent, or Firm* — Fish & Richardson P.C.

(57) ABSTRACT

The invention relates to methods for the early diagnosis of Acute Coronary Syndrome.

15 Claims, 7 Drawing Sheets

(56) References Cited

OTHER PUBLICATIONS

Magnani et al., "Myocarditis: Current Trends in Diagnosis and Treatment", Circulation, vol. 113:876-890 (2006).

Maisel et al., "Rapid Measurement of B-Type Natriuretic Peptide in the Emergency Diagnosis of Heart Failure", N Engl J Med., vol. 347:161-167 (2002).

McKie et al., "Defining high-sensitivity cardiac troponin concentrations in the community," Clinical Chemistry, vol. 59:1099-1107 (2013).

Noren et al., "Occurrence of myocarditis in sudden death in children", J Forensic Sci., vol. 22:188-196 (1977).

Pilz et al., "Small-Angle X-Ray Studies of the Human Immunoglobulin Molecule Kol", Eur. J. Biochem, vol. 75:195-199 (1977).

Rich, J., "Epidemiology, pathophysiology, and etiology of congestive heart failure in older adults", Am Geriatr Soc., vol. 45:968-974 (1997).

Sandoval et al., "The global need to define normality: the $99^{th}$ percentile value of cardiac troponin", Clin Chem, vol. 60:455-462 (2014).

Shields et al., An appraisal of polystyrene-(ELISA) and nitrocellulose-based (ELIFA) enzyme immunoassay systems using monoclonal antibodies reactive toward antigenically distinct forms of human C-reactive protein, J Immunol Methods, vol. 141:253-261 (1991).

Strunk et al., "Impact of the History of Congestive Heart Failure on the Utility of B-Type Natriuretic Peptide in the Emergency Diagnosis of Heart Failure: Results from the Breathing Not Properly Multinational Study", Am J Med, vol. 119:69.e1-69.e.11 (2006).

Thompson et al., "The physiological structure of human C-reactive protein and its complex with phosphocholine", Structure, vol. 7:169-177 (1999).

Thygesen et al., "Third Universal Definition of Myocardial Infarction", J Am Coll Cardiol, vol. 60:1581-1598 (2012).

Ying et al., "Identification and partial characterization of multiple native and neoantigenic epitopes of human C-reactive protein by using monoclonal antibodies", J Immunol, vol. 143:221-228 (1989).

\* cited by examiner

| Ischemic damage level | 12hr max fracCRP pos >59.47 | hr | corresponding TnI pos >0.50 | fracCRPxTnI pos >1.58 |
|---|---|---|---|---|
| 0 (non-cardiac, non-ACS) [N=20] | | | | |
| JT65F cp: MI ruled out | 13.62 | 0 | 0.01 | 0.14 |
| BC80F cp: orthostatic hypotension | 19.22 | 0 | 0.04 | 0.77 |
| DR52F cp: MI ruled out | 13.52 | 7.6 | 0.09 | 1.22 |
| RW77M sb: atrial fibrillation | 11.2 | 8 | 0.02 | 0.22 |
| MC53M cp: MI ruled out | 5.85 | 0 | 0.07 | 0.41 |
| PH61M cp: normal sinus rhythm | 10.95 | 7.9 | 0.07 | 0.77 |
| SL53M cp: MI ruled out | 19.78 | 5.4 | 0.08 | 1.58 |
| MC82F c,abd p: ACS ruled out | 10.65 | 0 | 0.02 | 0.21 |
| IC16F cp: atelectasis | 16.8 | 5 | 0.01 | 0.17 |
| MG33M cp: heroin withdrawal | 13.87 | 9.4 | 0.06 | 0.83 |
| FS80F c,La,Lj p: MI ruled out | 54.18 | 6.6 | 0.02 | 1.08 |
| RS54F cp: CHF with cardiomyopathy | 10.74 | 8.7 | 0.03 | 0.32 |
| DW53F cp: MI ruled out | 13.06 | 9.5 | 0.02 | 0.26 |
| KK81M cp: MI ruled out | 9.39 | 6.5 | 0.02 | 0.19 |
| EB68F cp: pneumonia (treated), COPD exacerbation | 5.26 | 0 | 0.01 | 0.05 |
| RA50M cp: negative for myocardial ischemia | 59.47 | 9.4 | 0.04 | 2.38 |
| WP84M cp: MI ruled out | 18.66 | 0 | 0.05 | 0.93 |
| CG60F cp: MI ruled out | 90.26 | 3.6 | 0.01 | 0.9 |
| MN74F cp: MI ruled out (status post-angioplasty) | 21.38 | 9.3 | 0.01 | 0.21 |
| DS58F cp: unlikely cardiac damage | 21.67 | 7.1 | 0.02 | 0.43 |
| % specificity | 95 (19/20) | | 0 (0/20) | 95 (19/20) |
| average hours to maximal fracCRP | | 5.2 | | |
| abd = abdominal; c = chest; La = left arm; Lj = left jaw; MI = myocardial infarction; p = pain; sb = shortness of breath | | | | |

FIGURE 1

| ischemic damage level | 12hr max fracCRP | hr | corresponding TnI | fracCRPxTnI |
|---|---|---|---|---|
| | pos >59.47 | | pos >0.50 | pos >1.58 |
| 1 (UA, &c) [N=14] | | | | |
| RB39M cp: unstable angina | 5.52 | 11.8 | 0.04 | 0.22 |
| JA58M La,cp: unstable angina | 14.47 | 0 | 0.01 | 0.14 |
| WE63M cp: unstable angina | 1.27 | 8.8 | 0.02 | 0.03 |
| CB44M cp: unstable angina | 2.52 | 0 | 0.15 | 0.38 |
| LK49M cp: unstable angina | 5.2 | 2.6 | 0.03 | 0.16 |
| HD72M ACS: unstable angina | 10.62 | 7 | 0.01 | 0.11 |
| FA70M cp: unstable angina | 126.88 | 0 | 0.05 | 6.34 |
| RW49M cp: unstable angina | 214.11 | 10.1 | 0.11 | 23.55 |
| AC74M STEMI: demand ischemia | 8.57 | 1.1 | 0.02 | 0.17 |
| SB46M cp: unstable angina | 984.55 | 2.9 | 0.02 | 19.69 |
| EM66F cp: unstable angina | 26.42 | 0 | 0.04 | 1.06 |
| HP08a46M cp: unstable angina | 87.47 | 7 | 0.02 | 1.75 |
| JD55M cp: increasing angina | 270.92 | 0 | 0.01 | 2.71 |
| WP78M cp: unstable angina | 44.77 | 7.4 | 0.04 | 1.79 |
| | | | | |
| 2 (NSTEMI, NSTE-ACS) [N=12] | | | | |
| TW50M cp: NSTEMI | 31.96 | 6.8 | 0.18 | 5.75 |
| PP77F n,s,cp: NSTEMI | 11.26 | 0 | 0.06 | 0.68 |
| FO82M cp: mild NSTEMI | 2.09 | 8.8 | 0.05 | 0.1 |
| CH86F w; cp: NSTEMI (hosp) | 2.1 | 0 | 0.07 | 0.15 |
| AU94F cp: ACS | 0.81 | 0 | 0.06 | 0.05 |
| HP0746M cp; wa,n; sb: NSTEMI | 44.67 | 5.9 | 0.1 | 4.47 |
| RO79M ACS: NSTEMI | 20.15 | 0 | 0.12 | 2.42 |
| JG58F cp: status post-MI (-40d) | 198.61 | 0 | 0.03 | 5.96 |
| IJ75F cp: possible ACS | 15.52 | 0 | 0.05 | 0.78 |
| WR74M cp: NSTEMI | 19.29 | 12.3 | 0.46 | 8.87 |
| EC90F cp; v-tach arr: NSTEMI | 65.68 | 7.2 | 0.06 | 3.94 |
| JL54M cp, depressive D/O: NSTEMI | 183.61 | 0 | 0.02 | 3.67 |
| | | | | |
| 3 (STEMI) [N=2] | | | | |
| DM68F lung mass; sb: STEMI | 7.23 | 0 | 0.03 | 0.22 |
| RV68F cp: STEMI (hosp) | 21.41 | 0 | 0.36 | 7.71 |
| | | | | |
| % sensitivity | 29 (8/28) | | 0 (0/28) | 50 (14/28) |
| average hours to maximal fracCRP | | 3.56 | | | a = arm; ACS = Acute Coronary Syndrome; c = chest; D/O = drug overdose;
La = left arm; MI = myocardial infarction; n = neck; NSTEMI = non-ST elevation MI;
p = pain; s = shoulder; sb = shortness of breath; STEMI = ST elevation MI;
UA = unstable angina; v-tach arr = ventricular tachycardia arrest; w = weakness

FIGURE 2

○ non-ACS ● UA (ID 1) ◆ NSTEMI (ID 2) ■ STEMI (ID 3)

FIG. 7

|  | ACS Positive (IDL 1-3) | ACS negative (IDL 0) | | |
|---|---|---|---|---|
| Test + (fracCRPxTnI >1.58) | 14 (TP) | 1 (FP) | Σ Test Positive (TP+FP) = 15 | Positive Predictive Value [TP/(TP+FP)] = 0.95 |
| Test − (fracCRPxTnI ≤1.58) | 14 (FN) | 19 (TN) | Σ Test Negative (FN+TN) = 33 | Negative Predictive Value [TN/(FN+TN)] = 0.58 |
|  | Σ Disease Positive = 28 | Σ Disease Negative = 20 | | |
|  | Sensitivity [TP/(TP+FN)] = 0.50 | Specificity [TN/(FP+TN)] = 0.95 | | |

METHODS FOR EARLY DIAGNOSIS OF ACUTE CORONARY SYNDROME

CLAIM OF PRIORITY

This application claims the benefit of U.S. Patent Application Ser. No. 61/060,729, filed on Jun. 11, 2008, the entire contents of which are hereby incorporated by reference.

TECHNICAL FIELD

This invention relates to methods for diagnosing acute coronary syndrome.

BACKGROUND

Acute coronary syndrome (ACS) is an umbrella term referring to a set of signs and symptoms, for example chest pain, that are results of a sudden decrease in blood flow to the heart (i.e., cardiac ischemia). ACS includes unstable angina, and two forms of heart attacks, non-ST elevation myocardial infarction (NSTEMI), and ST-elevation myocardial infarction (STEMI). About 1.5 million patients per year are diagnosed with ACS in the United States.

SUMMARY

The present invention is based, at least in part, on the discovery that plasma levels of fractional forms of C-reactive protein, interpreted in the context of certain cardiac markers, e.g., troponin I (TnI), can detect cardiac ischemic damage or ACS in a patient earlier than using the cardiac markers alone. Accordingly, provided herein are, inter alia, methods for early detection or diagnosis of ACS or cardiac ischemic damage in patients.

In general, the present invention provides methods for early diagnosis of acute coronary syndrome (ACS) or detecting cardiac ischemia in a subject. The methods include obtaining, e.g., measuring, a level of a cardiac specific marker, e.g. TnI, in the subject, obtaining a level of total C-reactive Protein (CRP) in the subject, obtaining a level of fractional forms of CRP (fracCRP) in the subject, calculating a normalized fracCRP value by dividing the fracCRP level by the total CRP level, calculating an interpretive score, e.g., by multiplying the normalized fracCRP value by the level of the cardiac specific marker, and comparing the interpretive score to a reference score, wherein a higher interpretive score than the reference score indicates that the subject has ACS or cardiac ischemia.

In some embodiments, the level of the cardiac specific marker, TnI, in the subject is provided. In those instances, the interpretive score can be calculated by multiplying the normalized fracCRP value by the TnI level. In some embodiments, the reference score for a fracCRP×TnI interpretive score is about 1.58, e.g., 1.53, 1.56, 1.58, 1.60, 1.62, 1.64, and/or 1.66. For example, a fracCRP×TnI interpretive score of greater than 1.58 is indicative of ACS or cardiac ischemic damage.

In some embodiments, the interpretive score is calculated by multiplying the normalized fracCRP value by the creatine kinase-MB (CK-MB) Index value in the subject.

In some embodiments, the methods include selecting a subject who has a TnI level that is below a first critical value. The first critical value can be, e.g., 0.4 ng/mL, 0.5 ng/mL, 0.6 ng/mL, and 0.7 ng/mL. In some embodiments, the first critical value is 0.5 ng/ml.

In other embodiments, the present methods include selecting a subject who has a creatine kinase-MB (CK-MB) Index value that is below a second critical value. In some embodiments, the second critical value is about 4.0 units.

The methods described herein can further include selecting a subject who does not have one of the following conditions: physical trauma, infectious disease, positive for or a history of using a cardiotoxic drug, or a level of total CRP that is greater than 25 mg/L. Physical trauma can include, e.g., blunt force trauma or serious wounds. Cardiotoxic drugs can include, for example, sympathomimetics such as amphetamines, methamphetamines, cocaine, phencyclidine, or ephedrine.

In some embodiments, the methods are useful for early diagnosis of three forms of ACS, including unstable angina (UA), non-ST elevation myocardial infarction (NSTEMI), and ST-elevation myocardial infarction (STEMI).

For the methods described herein, the levels of the cardiac marker, total CRP, and fracCRP in the subject are levels of these markers in samples, e.g., body fluid, e.g., blood, serum, or plasma, from the subject. In some embodiments, the subject is a human subject.

In another aspect, provided herein are methods for early diagnosis of ACS or detecting cardiac ischemia in a subject. The methods include obtaining a first level of a cardiac specific marker, a first level of total CRP, and a first level of fracCRP in the subject from a first time point, calculating a first normalized fracCRP value, e.g., by dividing the first fracCRP level by the first total CRP level, obtaining a second level of the cardiac specific marker, a second level of total CRP and a second level of fracCRP in the subject from a second time point, calculating a second normalized fracCRP value by dividing the second fracCRP level by the second total CRP level, obtaining a maximal normalized fracCRP value, wherein the maximal normalized fracCRP value is the higher value of the first and second normalized fracCRP values, calculating an interpretive score, e.g., by multiplying the maximal normalized fracCRP value by the level of a cardiac specific marker from the same time point that yielded the maximal normalized fracCRP value, and comparing the interpretive score to a reference score, wherein a higher interpretive score than the reference score indicates that the subject has ACS or cardiac ischemia. The cardiac specific marker can include, for example, TnI and CK-MB Index.

In some embodiments, the methods described here can include providing the levels of a cardiac specific marker, total CRP, and fracCRP in a subject from multiple time points, e.g., at least two, three, or more than three time points. The normalized fracCRP values can be determined for each time point, and the maximal normalized fracCRP value, e.g., the highest value, among these values can be determined, and used for calculating an interpretive score.

As used herein, a "sample" includes any bodily fluid or tissue, e.g., one or more of blood, serum, plasma, urine, and body tissue. In certain embodiments, a sample is a serum, plasma, or blood sample.

The term "fractional forms of CRP" ("fracCRP") includes all forms of CRP that can be recovered from bodily fluid or tissue by adherence to and release from a phosphorylcholine matrix. In some embodiments, only dimers and trimers are measured.

As used herein, "total CRP" includes all forms of CRP that can be measured from bodily fluid or tissue by any suitable immunoassay.

As used herein, an "interpretive score" is a value derived, e.g., calculated, from the level of fracCRP, e.g., expressed as a normalized fracCRP value, and the level of one or more cardiac markers in a patient. An interpretive score, therefore, takes into account the levels of fracCRP and the cardiac marker in a patient. An interpretive score is useful for making a diagnosis or treatment decision.

The term "reference score" refers to an empirically determined value based on data obtained from a population of ACS-positive and ACS-negative patients. The reference score, e.g., a cutoff value, can be any suitable reference score, including but not limited to the highest interpretive score among a group of ACS-negative patients, or the lowest interpretive score among a group of ACS positive patients, or a score that represents a value above which a subject is significantly more like to have ACS or cardiac ischemic damage. One of skill in the art will readily be able to select and apply a suitable reference score. Some exemplary reference scores are provided herein.

The terms "patient" and "subject" are used throughout the specification to describe an animal, e.g., a rodent or non-rodent, or a human, to whom treatment according to the methods of the present invention is provided. Veterinary and non-veterinary applications are contemplated. The term includes, but is not limited to, mammals, e.g., humans, other primates, pigs, rodents such as mice and rats, rabbits, guinea pigs, hamsters, cows, horses, cats, dogs, sheep and goats. Typical patients include humans, farm animals, horses, and domestic pets such as cats and dogs.

The methods described herein have a number of advantages. For example, the methods can be used to determine whether a subject with symptoms concerning ACS should be admitted or held as an inpatient for further assessment. The present methods can also be used to determine whether to treat a subject who has non-diagnostic EKG results or cardiac marker levels, with thrombolytic therapy or clot buster drugs to prevent a life-threatening heart attack. Better and earlier treatment decisions can lead to reduced morbidity and mortality. The methods described herein can be used to make general assessments as to whether a subject should be further tested to determine a specific diagnosis.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1 is a table showing data for patients who were diagnosed as negative for ACS. For each patient, the data shown in the table include: the maximal normalized fracCRP value (max fracCRP), hours post the first blood draw when the maximal fracCRP value was reached (hr), the TnI level of the sample that yielded the maximal normalized fracCRP value (corresponding TnI), and the calculated interpretive score based on the maximal normalized fracCRP value multiplied by the corresponding TnI value (fracCRP×TnI).

FIG. 2 is a table showing data for patients who were diagnosed as positive for ACS. This table includes the same kinds of data shown in the table of FIG. 1. UA=unstable angina, NSTEMI=non-ST elevation myocardial infarction, STEMI=ST-elevation myocardial infarction. Those frac-CRP×TnI values greater than 1.58 are in bold.

FIG. 7 is a table showing that the sensitivity and specificity of the fracCRP×TnI interpretive score for diagnosing ACS (as determined based on discharge summaries) were 50% and 95%, respectively. Each box of the table incorporates its own mathematical formula (as shown in each box) derived from the four basic parameters: true positive (TP; diagnosed as ACS-positive and had an fracCRP×TnI interpretive score >1.58), false positive (FP; diagnosed as ACS-negative and had an fracCRP×TnI interpretive score >1.58), false negative (FN; diagnosed as ACS-positive and had an fracCRP×TnI interpretive score ≤1.58) and true negative (TN; diagnosed as ACS-negative and had an fracCRP×TnI interpretive score ≤1.58).

DETAILED DESCRIPTION

Figure 3:
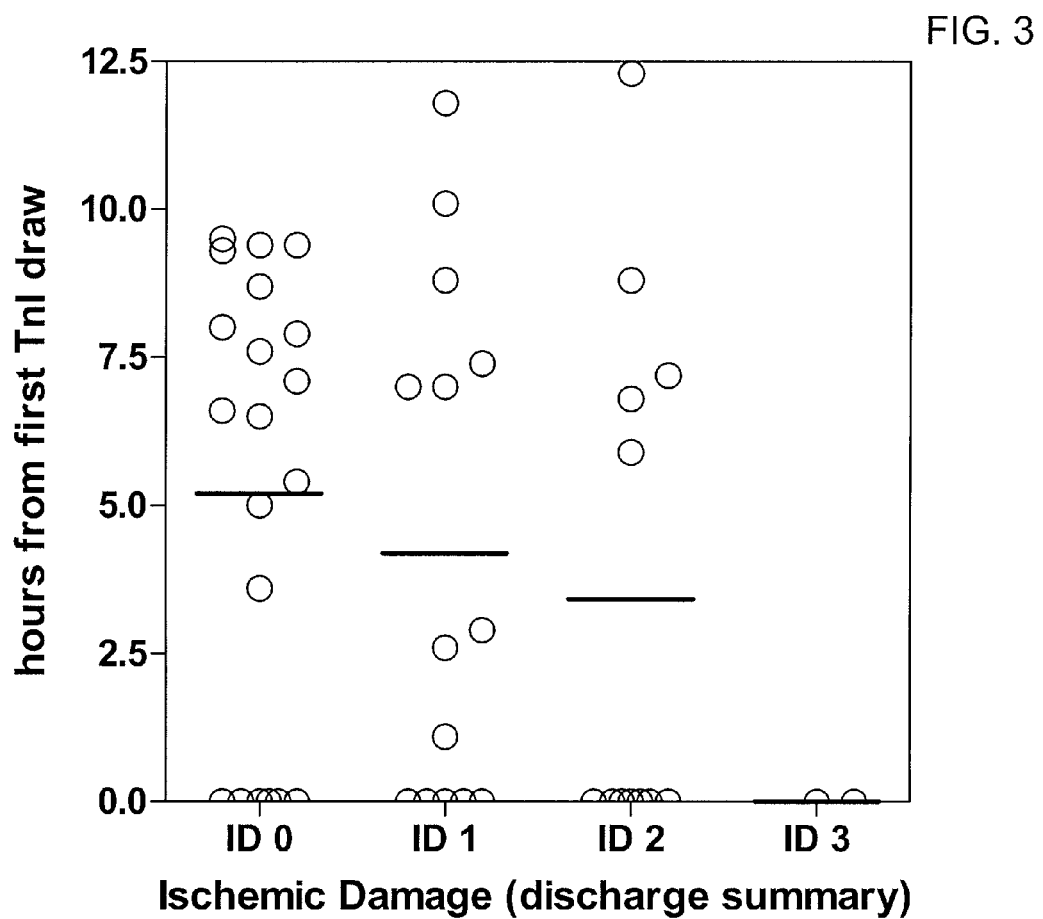
FIG. 3 is a graph showing the time interval in hours from the first blood draw until the maximal 12 hr fracCRP value was reached in the patients. The patients, each represented by an open circle, were grouped into four categories of cardiac ischemia or ACS based on their discharge summaries. The mean maximal normalized fracCRP value for each category is show (horizontal bar). ID 0=non-ACS; ID 1=unstable angina (UA); ID 2=non-ST elevation myocardial infarction (NSTEMI); ID 3=ST-elevation myocardial infarction (STEMI).

This invention is based, at least in part, on the discovery that plasma levels of fractional forms of CRP, interpreted in the context of cardiac markers, e.g., troponin I, can detect cardiac ischemic damage or ACS in a patient earlier than using the cardiac markers alone. Accordingly, provided herein are, inter alia, methods for early detection or diagnosis of ACS or cardiac ischemic damage in patients.

C-Reactive Protein (CRP)

Native C-reactive protein ("nCRP"), a marker of inflammation that is a planar pentameric arrangement of five identical 23 kDa subunits, exhibits calcium-dependent binding to phosphorylcholine ("PC") (Volanakis and Wirtz, Nature, 281:155-157 (1979)). In vivo, endothelial apoptotic processes culminate in exposure of phosphorylcholine groups on the membrane surface and capture of circulating native CRP (Kim et al. Ann NY Acad Sci. 987:68-78 (2003)). Once bound to PC, the pentameric ring of the human CRP opens, resulting in dissociation of the subunits into fractional forms, e.g., dimeric and trimeric forms (Wang and Sui, Biochem. Biophys. Res. Comm., 288:75-79 (2001)).

Total CRP levels have been shown in multiple prospective epidemiological studies to predict future cardiovascular disease, including myocardial infarction, stroke, peripheral arterial disease, sudden cardiac death and cardiovascular events in general (see, e.g., Ridker, Circulation, 107:363-369 (2003)).

Measuring Levels of Total CRP and Fractional Forms of CRP

The methods described herein involve measuring levels of total CRP and fracCRP in a subject to determine whether the subject has ACS.

Total CRP

The level of total CRP in a sample can be determined by techniques known in the art, e.g., immunoassays. Commercial immunoassays for CRP are readily available, such as ELISA-based assay kits from Diagnostic Systems Laboratories, Inc., Calbiotech, Inc., and ALerCHECK™ Inc.; or other assays, e.g., from Wako Chemicals USA, Inc. (turbidimetric immunoassay); Siemens Healthcare Diagnostics; Beckman Coulter, Inc., Randox Laboratories Ltd. (e.g., latex-enhanced immunoturbidimetric assay); Olympus America Diagnostics and Abbott Diagnostics. In general, a high-sensitivity CRP assay should be used, i.e., an assay with a detection range of about <1.0 mg/L to ≤about 10.0 mg/L.

FracCRP

The levels of fracCRP in a sample can be measured by methods known in the art. In general, fracCRP in a sample can first be captured and concentrated, e.g., using known capture and release methods. One exemplary method employs phosphorylcholine (PC)-conjugated agarose beads (Pierce, Rockville, Ill.) to capture substantially all of the CRP molecules (e.g., native and fractional forms) present in the sample. This can be followed by quantitative analysis of the forms separated by size exclusion chromatography (SEC), such as high performance liquid chromatography (HPLC) incorporating an SEC matrix, or capillary electrophoresis, e.g., under non-denaturing conditions.

One exemplary method for capturing fracCRP and measuring its level is described in Example 1 below. Another exemplary method includes the following steps: (1) Pour off plasma/serum from clinical specimen tube into a 1.5 mL microcentrifuge tube and microfuge at 16,000×g for 1 minute. Withdraw supernatant to a fresh microcentrifuge tube. (2) Transfer 50 μL of a 50% suspension of phosphorylcholine beads (#20307; Pierce Biotechnology Inc., Rockford Ill.) to a tube filter (e.g., Costar™ SpinX™-LC unit, No. 8169, Corning; 500 μL tube filter, 0.22 μm pore nylon membrane, 2.0 mL tube). Microfuge 1 minute and then pour off filtrate from tube. (3) Add to beads on tube filter 250 μL 4 mmol/L $CaCl_2$ in binding buffer (bb) [bb: 0.1 mol/L Tris (pH 7.5), 0.2 mol/L NaCl], followed by 250 μL plasma/serum specimen. Cap tube. (4) Mix specimen/bead suspension on a platform mixer for 10 minutes at ~25° C. (fracCRP forms appear to be preferentially captured in this method). Microfuge 1 minute and then pour off filtrate from tube. (5) Rinse beads×3 in 2 mmol/L $CaCl_2$ in bb (0.5 mL buffer/25 $mm^3$ beads). For each rinse, gently mix the contents of the tube filter, microcentrifuge for 1 minute, and pour off the filtrate. (6) Release bead-bound CRP with 25 μL enhanced-release buffer (erb) [0.02 mol/L $Na_2EDTA$, 0.1 mol/L Tris (pH 7.5), 1.5 mol/L KCl]. Incubate for 5 minutes at ~25° C., mixing (gently flicking tube) at 1 minute intervals. Microfuge 1 minute. Leave filtrate at bottom of tube. (7) Repeat release of bead-bound CRP with 25 μL erb, as before (step 6). Record the total volume of the released CRP, which should be approximately 50 μL, or ⅕ the original plasma/serum volume (i.e., 5× concentrate). (8) Run protein molecular weight standards, 1.35-670 kDa (Gel Filtration Standards, No. 151-1901; Bio-Rad Laboratories, Hercules Calif.) before each subject specimen series. (9) Inject via autosampler (508 Basic All-Electric Autosampler, Beckman Coulter) a 20 μL aliquot of released CRP (representing 0.1 mL-plasma/serum-equivalent) onto a 5-100 kDa range size-exclusion HPLC column (Bio-Sil SEC 125-5 Column, No. 125-0060; Bio-Rad Laboratories) equilibrated in the mobile phase [0.1 mol/L sodium phosphate (pH 7.45)], and fractionate at ~1 mL/minute (118 Isocratic Solvent Delivery Module, Beckman Coulter), recording absorbance at 215 nm (Model 166 Programmable Detector Module, Beckman Coulter) vs elution time. (10) Integrate peak areas of fracCRP (approximately 85 kDa major peak and any subsequent shoulder peak) via data analysis software (32 Karat Workstation, Beckman Coulter), expressing as Absorbance Units×elution time in minutes (AUm). Exclude any heavier peaks from the calculation.

All or parts of the methods for measuring fracCRP levels can be automated. For example, automated HPLC can be used.

Skilled practitioners will readily appreciate that a number of methods can be employed to measure fracCRP levels in samples, so long as the fracCRP in the samples retains its native conformation throughout the assay.

Cardiac Markers

Cardiac markers useful in the present methods can be associated with cardiac damage. For example, determining the level of a cardiac marker, e.g., the plasma level, in a subject can be useful for diagnosing myocardial infarction. Cardiac markers are known in the art, and include, but are not limited to, troponin I (TnI), troponin T (TnT), creatine kinase-MB (CK-MB), aspartate transaminase (AST), lactate dehydrogenase (LDH), ischemia-modified albumin (INA), alanine transaminase (ALT), and myoglobin (Mb). Among these, the troponin markers are considered to be the most sensitive and specific markers for cardiac damage. CK-MB is a particular isoenzyme of creatine kinase, and its level is typically expressed as a CK-MB Index (ratio of CK-MB to total creatine kinase). Levels of these cardiac markers can be determined by methods known in the art, e.g., immunoassays on subject plasma or serum samples.

TnI is an intracellular, compartmentalized protein—a myofilament component within the myofiber, and its release to the circulation occurs after loss of membrane integrity, irreversible cell damage and reperfusion (Van Eyk et al., Circ Res. 1998; 82:261-71). Release of TnI from myocardium is usually detected in circulation 4-6 hours after infarction, and the duration of the TnI cycle is about 3-10 days (Beckett et al., Cardiovascular disorders. In *Lecture Notes: Clinical Biochemistry*, $7^{th}$ ed. Oxford, UK:Blackwell Publishing, Ltd., 2005. Ch 11, pp 160-76). The TnI peak is usually reached about 12-24 hours after infarction. Id. In contrast, fracCRP appears much earlier in the circulation following tissue ischemia, usually peaking within 4 hours (FIG. 2 below). This earlier appearance is hypothesized to follow the exposure of phosphorylcholine groups in damaged tissue early in the ischemic process—the result of subsarcolemmal blebs and breaks in the plasma membrane (Steenbergen et al., Circ. Res. 60:478-486 (1987)).

About 80% of the subjects arriving at an Emergency Department (ED) with chest pain or similar pain symptoms that might be indicative of ACS have normal or non-diagnostic electrocardiogram (ECG) results. Such subjects are generally tracked for at least twelve hours using markers of cardiac damage, e.g., TnI and CK-MB, to gather additional diagnostic information, until a decision can be made for either more intensive follow-up or discharge. About 5% of these subjects are eventually diagnosed with ACS.

The results of these laboratory tests for TnI and CK-MB levels (both of which are generally immunoassays) are typically interpreted as a serial set. Generally, a TnI level above the critical value of 0.4 ng/ml is considered diagnostic of cardiac damage or ACS. Similarly, a CK-MB Index value above the critical value of 4.0 units is considered as indicative of ACS or cardiac damage. However, subjects with ACS or cardiac damage can have a TnI and/or CK-MB Index value that is below the critical value.

Elevations of TnI and/or CK-MB may indicate cardiac damage, not necessarily cardiac ischemic damage. Cardiac ischemic damage results from a lack of blood flow to the heart because of, e.g., blood clots. The list of conditions commonly associated with elevations of cardiac troponin in the absence of ischemic damage include acute pulmonary embolism, acute pericarditis, acute or severe heart failure, myocarditis, sepsis and/or shock, and renal failure (see, e.g., Roongsritong et al., *Chest*. 2004; 125:1877-84).

Methods for Diagnosing ACS or Cardiac Ischemic Damage

The methods described herein can be used to, inter alia, diagnose ACS or cardiac ischemic damage in a subject with normal or non-diagnostic EKG results or low elevated levels of cardiac markers, e.g., TnI and CK-MB.

FracCRP Levels

As noted above, native pentameric CRP (nCRP) can bind to phosphorylcholine (PC) moieties exposed on the cell surface membrane as a result of tissue damage. The PC-bound nCRP is biologically modified to fracCRP, with a relative molecular size of about 85 kDa by size exclusion HPLC. Accordingly, an elevated level of fracCRP in a subject can indicate tissue damage, e.g., cardiac ischemic damage.

Data described herein demonstrate that plasma elevations of fracCRP in response to a cardiac ischemic event occur much more quickly than do plasma elevations of TnI from the same event. Although many conditions resulting in significant acute tissue damage could cause elevation of fracCRP, the methods described herein interpret the fracCRP levels within the context of the concurrent level of a more cardiac-specific marker, e.g., troponin I (TnI) or the CK-MB Index (ratio of CK-MB to total CK). Accordingly, the methods described herein are useful for early detection of ACS or cardiac ischemic damage.

Methodology—Determining an Interpretive Score

The methods described herein include determining an interpretive score (IS) in a subject with symptoms indicative of ACS, and comparing that score to a predetermined reference score. If the interpretive score is higher than the reference score, it is indicative that the subject has ACS or cardiac ischemic damages.

Accordingly, the present methods include, inter alia, determining an interpretive score that takes into account the level of fracCRP, and the levels of one or more cardiac markers in a patient. An interpretive score allows a diagnosis or decision to be made based on a combination of fracCRP and cardiac marker levels. For example, the present methods can include, inter alia, determining the levels of fracCRP, e.g., a normalized fracCRP level, and a cardiac marker, e.g., TnI or CK-MB (expressed as a CK-MB Index), in a subject, and calculating an interpretive score based on these levels. An interpretive score can be calculated, e.g., by multiplying the fracCRP value, e.g., a normalized fracCRP value, by the cardiac marker value. The interpretive score is then compared to a predetermined reference score, e.g., a cutoff value. If the interpretive score is higher than the reference score, it is indicative that the subject has cardiac ischemic damage or ACS.

The reference score is determined empirically based on data obtained from ACS-positive and ACS-negative patients. The reference score, e.g., a cutoff value, is the highest interpretive score among a group of ACS-negative patients. The sensitivity and the specificity of the reference score for diagnosing ACS can be determined using statistical methods known in the art.

In some embodiments, the reference score calculated based on fracCRP and TnI values is about 1.58, e.g., 1.53, 1.56, 1.58, 1.6, 1.62, 1.64, and 1.66.

For example, if the interpretive score calculated by multiplying a fracCRP value by a TnI value for a patient is greater than 1.62, e.g., about 1.63, more than 2, about 2.8, more than 4, or more than 8, it can be indicative that the subject has cardiac ischemic damage or ACS.

The level of total CRP (i.e., combined level of native CRP and fracCRP) in a subject can also be determined. In that case, it may be useful to calculate a normalized fracCRP level in that subject by dividing the fracCRP level by the total CRP level. The resulting normalized fracCRP level can then be used to calculate an interpretive score as described above, e.g., by multiplying the normalized fracCRP value by the TnI value and/or some other cardiac marker value.

Multiple samples from a subject from different time points can be analyzed to determine an interpretive score. For example, samples can be obtained from the subject at regular intervals, e.g., every 4 hours, in a period of, e.g., 12 hours. The levels of a cardiac marker, fracCRP, and total CRP can be determined for each sample. A normalized fracCRP value (i.e., fracCRP/total CRP) can then be determined for each sample. The highest normalized fracCRP value and the cardiac marker values from the same sample can be used to calculate an interpretive score.

The methods described herein are useful in a wide variety of clinical contexts. For example, the methods can be used for diagnosing subjects in hospitals and outpatient clinics, as well as the Emergency Department. The methods can be carried out on-site or in an off-site laboratory.

Once it has been determined that a subject has an interpretive score above a predetermined reference score, the information can be used in a variety of ways. For example, if the subject has an elevated score, e.g., as compared to a reference score, a decision to treat aggressively can be made, and the subject can be, e.g., admitted to a hospital for treatment as an inpatient, e.g., in an acute or critical care department. Triage decisions, e.g., in an ED or other clinical setting, can also be made based on information provided by a method described herein. For example, those subjects with high scores can be prioritized over those with lower scores, or a decision to administer a specific treatment or to treat more aggressively, can be made.

Patient Population

Although the methods described herein can be used for any patient, at any time, they are particularly useful for those patients for whom a diagnosis, or the severity of a condition associated with cardiac ischemia, is difficult to determine. For example, a patient may have symptoms suggesting ACS, e.g., chest pain, nausea, and/or shortness of breath, but have normal or non-diagnostic EKG results, or a level of a cardiac marker, e.g., TnI and/or CK-MB, that is below what is considered as critical or diagnostic. For such patients, the methods described herein can be used for early diagnosis of ACS.

Having a TnI level and/or a CK-MB Index value exceeding a critical value can be considered diagnostic for cardiac damage or ACS. For these patients, it may not be necessary to employ the present methods for making a diagnosis or treatment decision. In some embodiments, the critical value for TnI is 0.4 ng/mL. In other embodiments, the critical value for CK-MB Index is 4.0 units.

Skilled practitioners can readily appreciate that the methods described herein may not be suitable for certain patients. For example, a patient with obvious physical trauma, e.g., blunt force trauma or wounds, would be expected to have an highly elevated level of CRP due to tissue damage not related to cardiac ischemia or ACS. Similarly, patients with infectious diseases (e.g., pneumonia), or who test positive for or have a history of using cardiotoxic drugs (e.g., amphetamines, methamphetamines, cocaine, phencyclidine or ephedrine) have been found to have elevated levels of fracCRP unrelated to ACS.

EXAMPLES

Example 1

A Retrospective Clinical Study

This example describes a retrospective clinical study demonstrating that an interpretive score calculated using the TnI level and the normalized fracCRP level (i.e., fracCRP/total CRP) in a patient is sensitive and specific for detecting or ruling out ACS in the patient within 12 hours of arrival. The data described herein also shows that the fracCRP×TnI interpretive score is unexpectedly more sensitive for early diagnosis of ACS than either TnI level or normalized fracCRP level alone.

Patient Selection

Plasma samples from patients were analyzed in this study. The study included patients who came to the UMass Memorial Medical Center with symptoms suggesting ACS, and had blood samples analyzed for cardiac markers. These patients has multiple samples drawn at different time points. Patient inclusion and exclusion criteria are listed in Table 1. Only patients with a TnI level less than the method's critical value of 0.5 ng/mL were included. Patients having obvious trauma, infectious diseases, and positive test results for a cardiotoxic drug were excluded from the study, as these factors can lead to a high level of total CRP and/or fracCRP independent of ACS or cardiac ischemia. Patients with a level of total CRP greater than 25 mg/L were also excluded.

TABLE 1

| Inclusion Criteria | Exclusion Criteria |
| --- | --- |
| Symptoms concerning for ACS (e.g., chest pain) | Obvious trauma |
| | Infectious disease |
| At least the first three samples each having a TnI level below 0.5 ng/mL | Positive for a cardiotoxic drug |
| | Level of total CRP >25 mg/L |
| No fracCRP analysis beyond a critical TnI result | |

The samples from the patients were identified by a data-mining algorithm. The identified samples were recovered before the 7-day discard point, and assayed using the methods described below. With permission from the Institutional Review Board (IRB), the discharge summaries and cardiac catheterization reports (if available) of the patients were analyzed to group the patients into four categories: ACS-negative (ischemic damage level 0; ID 0), and three ACS-positive groups including unstable angina (UA; ID 1), non-ST elevation myocardial infarction (NSTEMI; ID 2), and ST-elevation myocardial infarction (STEMI; ID 3).

Materials and Methods

Capture of Biologically Active CRP

Plasma from the clinical specimen tube was removed and put into a 1.5 mL microcentrifuge tube, and microfuged at 16,000×g for one minute. The supernatant was removed to a fresh microcentrifuge tube. A 0.25 mL aliquot of plasma or serum was diluted with an equal volume of 4 mmol/L $CaCl_2$ in binding buffer (bb) [0.1 mol/L Tris (pH 7.5), 0.2 mol/L NaCl], and added to phosphorylcholine-coated beads pelleted from 50 µL of a 50% suspension (#20307; Pierce Biotechnology, Inc., Rockford Ill.). The specimen/bead suspension was mixed on a platform mixer for one hour at 25° C. FracCRP forms appeared to be preferentially captured. The beads with captured CRP were washed 3 times in 2 mmol/L $CaCl_2$ in 1 mL binding buffer/25 $mm^3$ beads. Each washing step was performed for 5 minutes at 25° C. on the platform mixer.

Release/Concentration of Captured CRP

Captured CRP was released from the beads by incubating the beads in a volume of enhanced-release buffer (erb, 0.02 mol/L $Na_2EDTA$, 0.1 mol/L Tris (pH 7.5), 1.5 mol/L KCl) equivalent to that of the beads (e.g., 25 µL erb/25 $mm^3$ beads) for 10 minutes at 25° C., mixing by gently flicking the tube at 1 minute intervals. The erb was removed to another tube, and the beads were again incubated as before with erb to recover any residual captured CRP or released CRP. The second volume of erb was pooled with the first. The total volume of CRP-containing erb was recorded, and was approximately 0.05 mL, or ⅕ of the original volume of the plasma/serum sample (e.g., about 5× concentration of CRP).

Size-Exclusion Chromatography of Released CRP

Protein molecular weight standards, 1.35-670 kDa (Gel Filtration Standards, No. 151-1901; Bio-Rad Laboratories, Hercules Calif.) were run before each series of patient samples. A 20 µL aliquot of released CRP (representing 0.1 mL-plasma/serum-equivalent) was manually injected onto a 5-100 kDa range size-exclusion HPLC column (Bio-Sil SEC 125-5 Column, No. 125-0060; Bio-Rad Laboratories) equilibrated in the mobile phase (0.1 mol/L sodium phosphate, pH 7.45), and fractionated at about 1 mL/minute (Waters 510 Solvent Delivery System, Millipore, Milford Mass.), recording absorbance at 215 nm (Waters 484 Tunable Absorbance Detector, Millipore, Milford Mass.) vs elution time. Peak areas of fracCRP from a chart record (Fisher Recordall® Series 5000, Houston Instrument, Austin Tex.) were integrated and expressed as Absorbance Units×elution time in minutes (AUm). Heavier peaks, if present, were excluded from the calculation. The fracCRP value was converted to AUm/L plasma.

Normalization of fracCRP Value and Conversion to Interpretive Score

Total CRP was determined on the immunochemistry system IMMAGE® 800 (CRP Ultra; Beckman Coulter, Inc., Fullerton Calif.). The fracCRP value was divided by the total CRP level (mg/L) for the same sample to yield a normalized fracCRP value (AUm/mg CRP) for the sample. For any given series of samples from a patient, the highest normalized fracCRP value and the TnI value or the CK-MB Index value from the same sample that yielded the highest normalized fracCRP value were used to calculate an interpretive score for determination of cardiac ischemia in that patient. The interpretive score was calculated by multiplying the normalized fracCRP value by the TnI value or the CK-MB Index value.

Results

Samples from 48 patients who met the inclusion criteria shown in Table 1 were analyzed using the methods described above. Discharge summaries were available for all 48 patients, and cardiac catheterization reports were available for 18 patients.

FIG. 1 shows the data for 20 ACS-negative patients. FIG. 2 presents the data for 28 ACS-positive patients.

The mean time intervals were determined from the first blood draw until the maximal fracCRP value within 12 hours was reached in the patients. As detailed in FIG. 3, the mean time interval (horizontal bar) were 5.2 hours for ACS-negative (ID0) patients, and an average 3.56 hours for ACS-positive patients (ID2, ID2, and ID3)). The maximal normalized fracCRP value was calculated on the initial draw in 30% of the ACS-negative cases, and in 50% of the ACS-positive cases.

Figure 4:
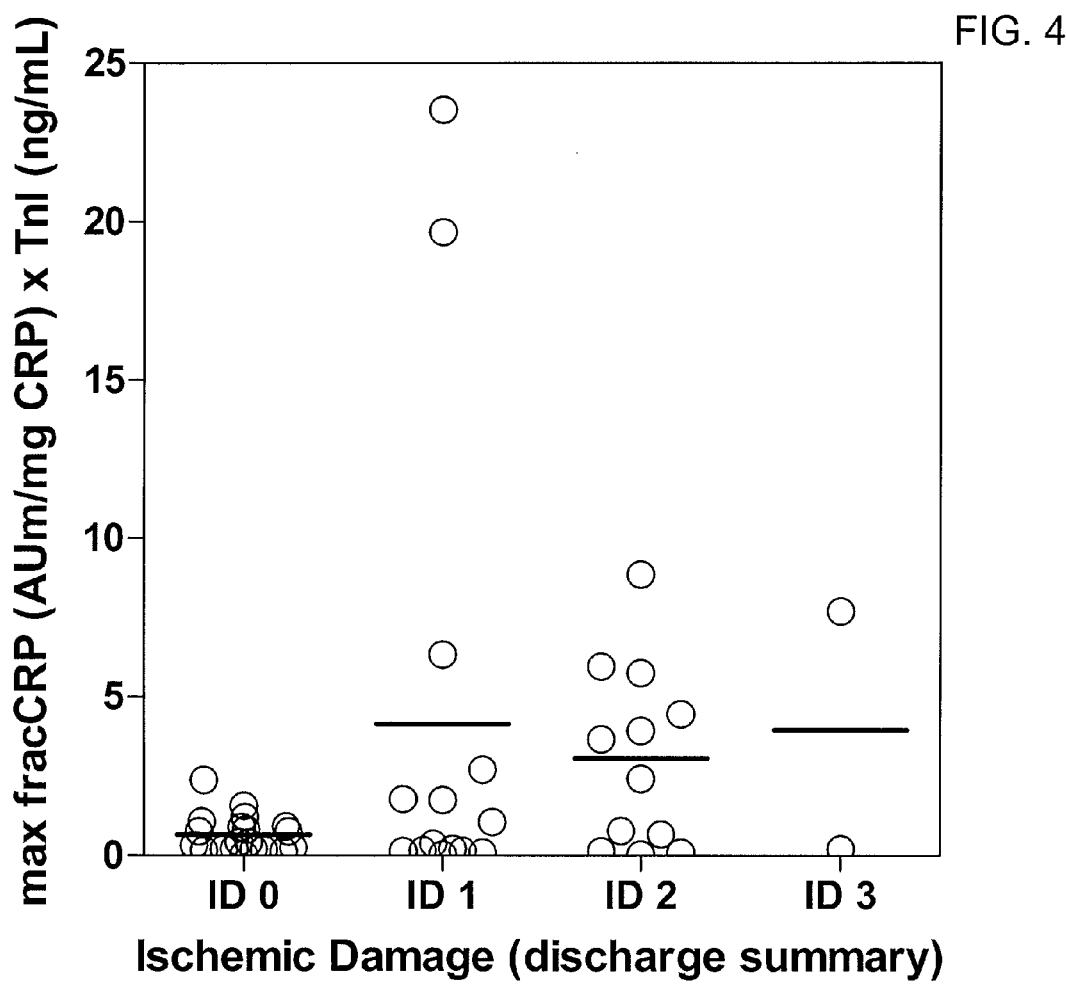
FIG. 4 is a graph showing the fracCRP×TnI interpretive scores for the patients by ACS categories. The means for all categories are shown by the horizontal bars.

By multiplying the maximal normalized fracCRP value by the TnI value, an interpretive score was determined for each patient (see FIGS. 1 and 2). As shown in FIG. 4, the mean interpretive scores for all ACS-positive categories (ID 1-3) were higher than that for the ACS-negative category (ID 0).

Figure 5A:
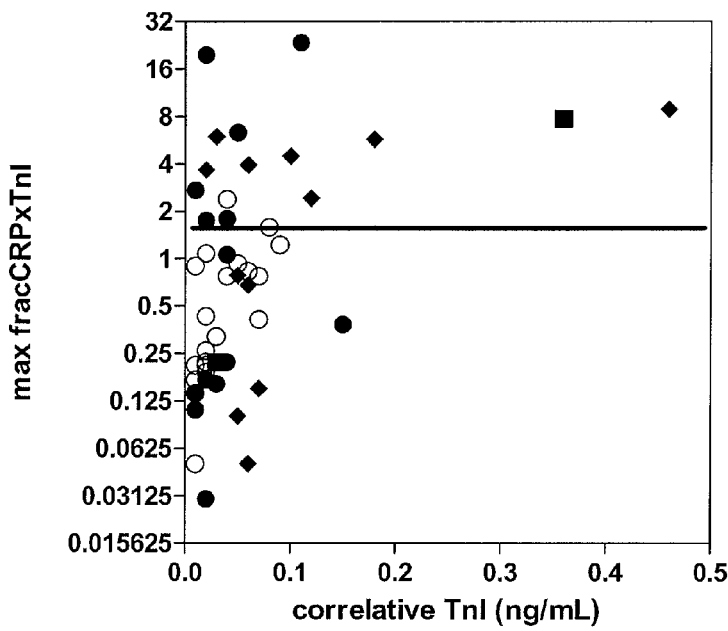
FIG. 5A is a graph showing the fracCRP×TnI interpretive score for each patient plotted against its respective TnI value. Open circles=ID 0 patients, filled circles=ID 1 patients, filled diamonds=ID 2 patients, filled squares=ID 3 patients.
Figure 5B:
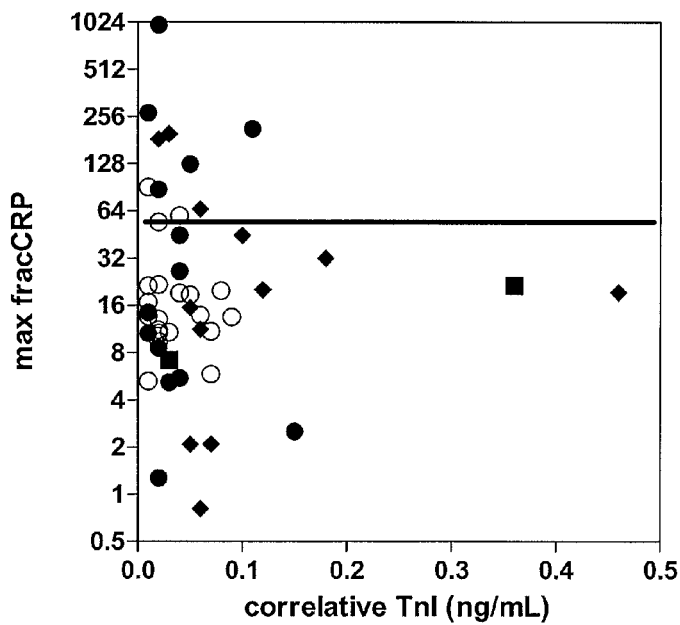
FIG. 5B is a graph showing the maximal normalized frac-CRP value for each patient plotted against its respective TnI value. Open circles=ID 0 patients, filled circles=ID 1 patients, filled diamonds=ID 2 patients, filled squares=ID 3 patients.

A reference or cut-off interpretive score was then determined empirically. The highest interpretive score (fracCRP× TnI), 1.58, among 95% of the ACS-negative (ID 0) patients was determined to be the cut-off value. In FIG. 5A, this cut-off interpretive score is indicated by the horizontal bar. For fracCRP alone, this cutoff is 59.47 (FIG. 5B). One observation, depicted in FIGS. 2 and 5B, is that at the time the normalized fracCRP value was maximal, none of the ACS-positive patients had a TnI level greater than the method's critical value of 0.50 ng/mL, and 11 (39%) ACS-positive patients had a TnI level that was within the normal range (less than 0.04 ng/mL). That is, at the time the normalized fracCRP value was maximal for these 11 patients, their TnI levels would not in themselves have indicated ACS. Of these 11 patients, three, who were finally diagnosed for UA (ID 1) and two, who were finally diagnosed with NSTEMI (ID 2), had an interpretive score greater than 1.58 (see FIG. 2, patients designated SB46M, HP08a46M, JD55M, JG58F, and JL54M).

Figure 6:
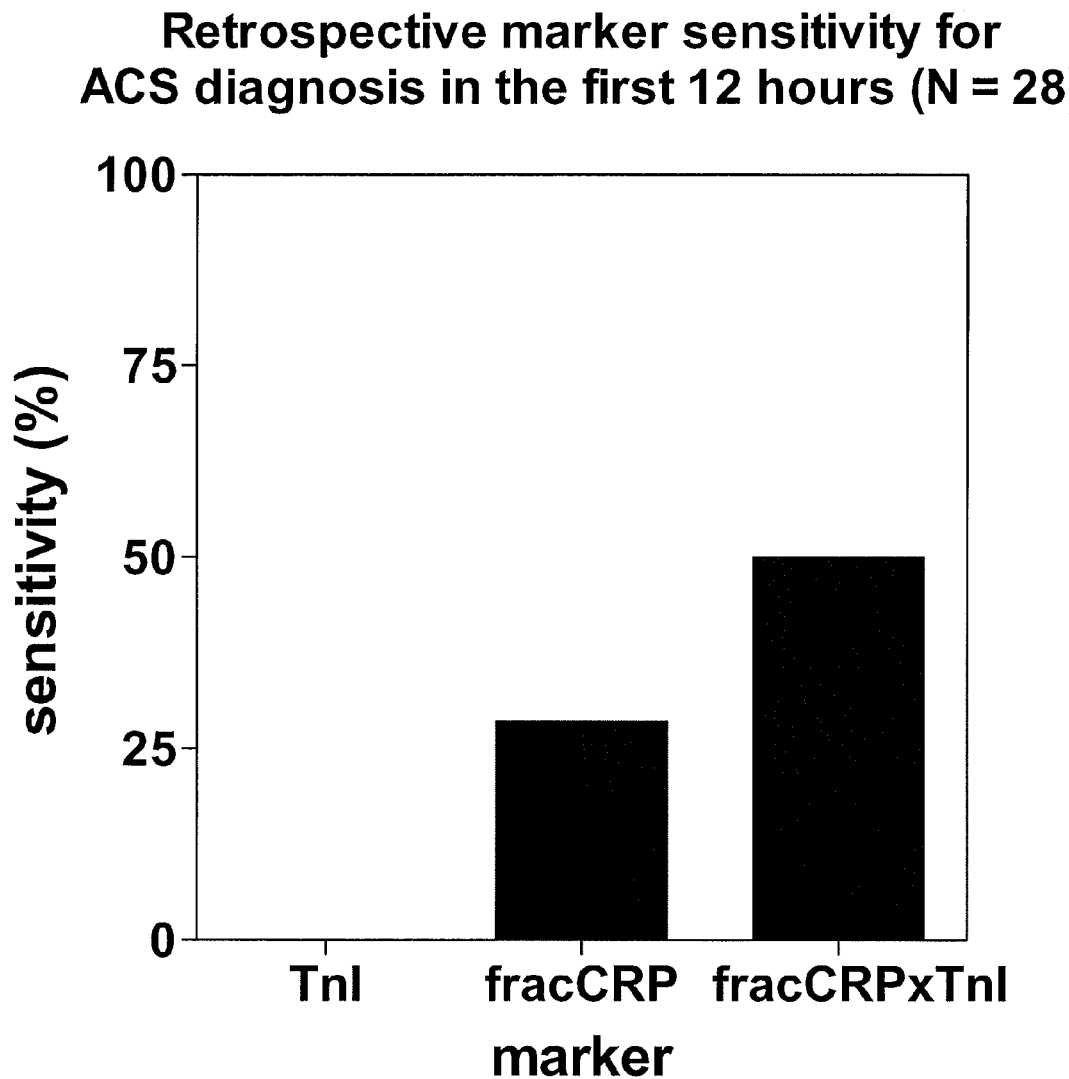
FIG. 6 is a bar graph showing the sensitivity of the TnI level, the fracCRP level and the fracCRP×TnI interpretive score for diagnosing ACS in the first 12 hours (determined based on their discharge summaries). For TnI alone, a positive test was defined by a cutoff score ≥0.4 ng/mL (Antman et al., N. Engl. J. Med. 335:1342-1349 (1996)). For fracCRP alone, a positive test was defined by a cutoff score >59.47.

The sensitivities of the TnI value, the normalized fracCRP value, and the interpretive score (fracCRP×TnI) for diagnosing ACS within 12 hours of the initial blood draw were compared (FIG. 6). There were no instrument-critical TnI results observed within this interval, so the TnI sensitivity was 0%. However, 29% of the 28 eventually diagnosed ACS-positive patients were identified within 12 hours by their fracCRP values (>59.47) alone, and 50% were identified by their interpretive scores (>1.58). The table in FIG. 7 characterizes the interpretive score for ACS (based on discharge summaries) in terms of the standard laboratory test parameters of sensitivity, specificity, and positive and negative predictive values. Cardiac catheterization reports, when available, were taken into consideration in the discharge diagnoses.

This data presented herein demonstrates that an interpretive score calculated based on the TnI value and the normalized fracCRP value of a patient can be used for early detection of ACS or cardiac ischemia.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for early diagnosis of acute coronary syndrome (ACS) in a human subject who has one or more symptoms of ACS, the method comprising:
   a) providing a sample comprising blood from a human subject suspected of having ACS obtained within 12 hours of arrival at a medical center;
   b) performing an immunoassay to determine a level of Troponin I (TnI) in a sample obtained from the human subject within 12 hours of arrival at a medical center;
   c) performing additional diagnostic analysis on the sample if the Troponin I (TnI) level is less than 0.04 ng/ml, wherein the additional diagnostic analysis comprises:
   contacting the sample obtained from the human subject with phosphorylcholine (PC) under conditions sufficient for binding of C-reactive protein (CRP) to the PC to occur in the sample;
   isolating the PC-bound CRP in the sample;
   fractionating the PC-bound CRP based on size;
   determining a level of one or more of the fractions of CRP in the sample (fracCRP) representing the level of CRP molecules that are not in the native pentameric ring form;
   calculating, using a suitably programmed computer, an interpretive score by multiplying the level of fracCRP by the level of TnI;
   comparing the interpretive score to a reference score, and
   diagnosing a subject who has a higher interpretive score than the reference score with ACS.

2. The method of claim 1, wherein ACS includes unstable angina (UA), non-ST elevation myocardial infarction (NSTEMI), and ST-elevation myocardial infarction (STEMI).

3. The method of claim 1 wherein the levels of TnI and the fracCRP are serum, blood, or plasma levels.

4. A method for early diagnosis of acute coronary syndrome (ACS) in a human subject who has one or more symptoms of ACS, the method comprising:
   a) providing a first sample comprising blood from a human subject suspected of having ACS within 12 hours of arrival at a medical center;
   b) performing an immunoassay to determine a first level of Troponin I (TnI) in a first sample obtained from the human subject at a first time point that is within 12 hours of arrival at a medical center;
   c) performing additional diagnostic analysis on the sample if the Troponin I (TnI) level is less than 0.5 ng/ml, wherein the additional diagnostic analysis comprises:
   contacting the first sample obtained from the human subject with phosphorylcholine (PC) under conditions sufficient for binding of C-reactive protein (CRP) to the PC to occur in the sample;
   isolating the PC-bound CRP;
   fractionating the PC-bound CRP based on size;
   determining a first level of one or more of the fractions of CRP in the sample (fracCRP) representing the level of CRP molecules that are not in the native pentameric ring form;
   d) providing a second sample comprising blood from the same human subject suspected of having ACS at a second time point that is also within 12 hours of arrival at a medical center;
   e) performing an immunoassay to determine a second level of TnI in a second sample obtained from the human subject at a second time point that is also within 12 hours of arrival at a medical center;

f) performing additional diagnostic analysis on the sample if the troponin I (TnI) level is less than 0.5 ng/ml, wherein the additional diagnostic analysis comprises:

contacting the second sample obtained from the human subject with phosphorylcholine (PC) under conditions sufficient for binding of C-reactive protein (CRP) to the PC to occur in the sample;

isolating the PC-bound CRP in the second sample;

fractionating the PC-bound CRP based on size;

determining a second level of one or more of the fractions of CRP in the sample (fracCRP) representing a second level of CRP molecules that are not in the native pentameric ring form;

g) determining a maximal fracCRP value calculated by taking the higher value of the first and second fracCRP levels;

h) calculating, using a suitably programmed computer, an interpretive score by multiplying the maximal fracCRP value by the level of TnI;

comparing the interpretive score to a reference score, and i) diagnosing a subject who has a higher interpretive score than the reference score with ACS.

5. The method of claim 4, wherein ACS includes unstable angina, non-ST elevation myocardial infarction (NSTEMI), and ST-elevation myocardial infarction (STEMI).

6. The method of claim 4, wherein the levels of TnI and fracCRP are blood, plasma, or serum levels.

7. The method of claim 1, wherein the one or more symptoms of ACS are chest pain or shortness of breath.

8. A method for treating acute coronary syndrome (ACS) in a human subject who has one or more symptoms of ACS, the method comprising:

performing an immunoassay to determine a level of Troponin I (TnI) in a sample obtained from the human subject within 12 hours of arrival at a medical center;

determining a level of CRP molecules that are not in the native pentameric ring form (fractional forms of CRP or fracCRP) in the sample by contacting the sample with phosphorylcholine to capture substantially all of the CRP molecules present in the sample, and determining the quantity of fracCRP by high performance liquid chromatography (HPLC);

calculating an interpretive score by multiplying the level of fracCRP by the level of TnI;

comparing the interpretive score to a reference score, diagnosing a subject who has a higher interpretive score than the reference score with ACS; and treating the subject for ACS.

9. The method of claim 8, wherein the one or more symptoms of ACS are chest pain or shortness of breath.

10. The method of claim 1, wherein the phosphorylcholine is conjugated to agarose beads.

11. The method of claim 1, wherein determining the quantity of CRP that is not in native pentameric ring form comprises separating CRP in the sample by size, and quantifying the amount of CRP that has a relative molecular size of about 85 kDa or less.

12. The method of claim 11, wherein quantifying the amount of CRP that has a relative molecular size of about 85 kDa or less is done using size exclusion high performance liquid chromatography (SE-HPLC).

13. The method of claim 1, wherein the CRP molecules that are not in the native pentameric ring form comprise open rings, dimeric, and trimeric forms of CRP.

14. The method of claim 4, wherein the CRP molecules that are not in the native pentameric ring form comprise open rings, dimeric, and trimeric forms of CRP.

15. The method of claim 8, wherein the CRP molecules that are not in the native pentameric ring form comprise open rings, dimeric, and trimeric forms of CRP.

\* \* \* \* \*